United States Patent
Mackinnon et al.

(10) Patent No.: US 12,033,723 B2
(45) Date of Patent: Jul. 9, 2024

(54) METHODS FOR PROTEOME DOCKING TO IDENTIFY PROTEIN-LIGAND INTERACTIONS

(71) Applicant: Cyclica Inc., Toronto (CA)

(72) Inventors: Stephen Scott Mackinnon, Burlington (CA); Leonard David Morayniss, Toronto (CA); Jason Mitakidis, Oakville (CA); Fuad G. Gwadry, Calgary (CA)

(73) Assignee: Cyclica Inc., Toronto (CA)

( * ) Notice: Subject to any disclaimer, the term of this patent is extended or adjusted under 35 U.S.C. 154(b) by 830 days.

(21) Appl. No.: 16/067,465

(22) PCT Filed: Dec. 31, 2015

(86) PCT No.: PCT/CA2015/051384
§ 371 (c)(1),
(2) Date: Jun. 29, 2018

(87) PCT Pub. No.: WO2017/113004
PCT Pub. Date: Jul. 6, 2017

(65) Prior Publication Data
US 2019/0018924 A1    Jan. 17, 2019

(51) Int. Cl.
*G16B 20/30*    (2019.01)
*G16B 5/00*    (2019.01)
(Continued)

(52) U.S. Cl.
CPC ............... *G16B 20/30* (2019.02); *G16B 5/00* (2019.02); *G16B 15/00* (2019.02); *G16B 15/30* (2019.02);
(Continued)

(58) Field of Classification Search
CPC ........ G16C 20/70; G16C 20/60; G16B 15/30; G16B 20/30; G16B 5/00; G16B 15/00;
(Continued)

(56) References Cited

U.S. PATENT DOCUMENTS

2002/0072887 A1    6/2002  Szalma et al.
2007/0016376 A1*   1/2007  Sato .................. G16B 15/00
                                                702/19
(Continued)

FOREIGN PATENT DOCUMENTS

JP    2003535394 A    11/2003
JP    2008217594 A     9/2008
(Continued)

OTHER PUBLICATIONS

International Search Report issued in corresponding application No. PCT/CA2015/051384 mailed Sep. 9, 2016 (3 pages).
(Continued)

*Primary Examiner* — Jesse P Frumkin
(74) *Attorney, Agent, or Firm* — Keller Preece PLLC

(57) ABSTRACT

The invention involves a method for identifying a target protein. The invention involves receiving a request to identify a target protein based on a ligand; identifying, using the ligand, a first protein, where the ligand binds with the first protein to form a ligand-protein complex; generating, a first binding site profile for the first protein, where the first binding site profile describes molecular properties of the first protein; obtaining, from a controlled server, structure data describing molecular properties of surfaces for a multitude of proteins, where the multitude of proteins comprises the target protein; identifying, using the first binding site profile and the structure data, the target protein; and presenting the target protein to a user.

16 Claims, 10 Drawing Sheets

(51) Int. Cl.
  *G16B 15/00*    (2019.01)
  *G16B 15/30*    (2019.01)
  *G16B 20/00*    (2019.01)
  *G16B 35/00*    (2019.01)
  *G16B 35/20*    (2019.01)
  *G16B 50/00*    (2019.01)
  *G16B 50/10*    (2019.01)
  *G16B 50/30*    (2019.01)
  *G16B 99/00*    (2019.01)
  *G16C 20/60*    (2019.01)

(52) U.S. Cl.
  CPC ............. *G16B 20/00* (2019.02); *G16B 35/00* (2019.02); *G16B 35/20* (2019.02); *G16B 50/00* (2019.02); *G16B 50/10* (2019.02); *G16B 50/30* (2019.02); *G16B 99/00* (2019.02); *G16C 20/60* (2019.02)

(58) Field of Classification Search
  CPC ........ G16B 20/00; G16B 35/00; G16B 35/20; G16B 50/00; G16B 50/10; G16B 50/30; G16B 99/00; G01N 2570/00
  See application file for complete search history.

(56) References Cited

U.S. PATENT DOCUMENTS

| | | | | |
|---|---|---|---|---|
| 2010/0312538 | A1* | 12/2010 | Umeyama | G16C 20/64 703/12 |
| 2015/0134266 | A1* | 5/2015 | Cardozo | A61K 31/343 702/19 |
| 2015/0324546 | A1* | 11/2015 | Dakshanamurthy | G16H 70/40 705/2 |
| 2017/0010229 | A1* | 1/2017 | Moritz | G01N 33/6848 |
| 2017/0147743 | A1* | 5/2017 | Bixby | G16C 20/50 |
| 2018/0080913 | A1* | 3/2018 | Zhang | G16B 35/00 |
| 2020/0357480 | A1 | 11/2020 | Mackinnon et al. | |
| 2022/0051759 | A1 | 2/2022 | Brereton et al. | |
| 2022/0108766 | A1 | 4/2022 | Mackinnon et al. | |

FOREIGN PATENT DOCUMENTS

| | | |
|---|---|---|
| JP | 2009151406 A | 7/2009 |
| WO | 2001085915 A2 | 11/2001 |
| WO | 2009064015 A1 | 3/2011 |
| WO | 2016200681 A1 | 12/2016 |

OTHER PUBLICATIONS

Written Opinion of the International Searching Authority issued in corresponding application No. PCT/CA2015/051384 mailed Sep. 9, 2016 (3 pages).

Extended European Search Report relating to European Patent Application No. 15911664.9 dated Jun. 8, 2020, 9 pages.

Barbara Zarzycka et al.; "Discovery of Small Molecule CD40-TRAF6 Inhibitors", Journal of Chemical Information and Modeling; vol. 55, No. 2, Jan. 27, 2015, pp. 294-307.

Didier Rognan; "Proteome-scale docking: myth and reality", Drug Discovery Today: Technologies, vol. 10, No. 3, Sep. 1, 2013, pp. e403-e409.

Shao-Xing Dai et al.; "Proteome—wide prediction of targets for aspirin: new insight into the molecular mechanism of aspirin", PeerJ, vol. 4, Jan. 1, 2016, pp. 1-20.

Notice of Reason for Rejection relating to Japanese Patent Application No. 2018-553273 dated Mar. 3, 2021, 13 pages.

Office Action relating to Canadian Patent Application No. 3,010,226 dated Nov. 9, 2021, 6 pages.

First Office Action relating to Chinese Patent Application No. 2015800858462 dated Jun. 3, 2021, 7 pages.

\* cited by examiner

METHODS FOR PROTEOME DOCKING TO IDENTIFY PROTEIN-LIGAND INTERACTIONS

BACKGROUND

The top chemogenomic mapping and protein target identification methods to identify protein-ligand interactions employ Quantitative Structure—Activity Relationships (QSAR) and pharmacophore modeling. These methods employ machine learning to compare a query ligand to databases of known ligands, assuming that structural similarities in the drugs themselves correspond to similarities in biological activity (for example, biological targets, toxicity, efficacy, etc.). Protein-ligand interaction mapping based on structural data are generally limited to select receptor scaffolds and/or drug scaffolds.

SUMMARY

In general, in one aspect, embodiments relate to a method for identifying a target protein. The method includes receiving a request to identify a target protein based on a ligand. The method further includes identifying, using the ligand, a first protein, where the ligand binds with the first protein to form a ligand-protein complex. The method further includes generating a first binding site profile for the first protein, where the first binding site profile describes molecular properties of the first protein. The method further includes obtaining, from a controlled server, structure data describing molecular properties of surfaces for a multitude of proteins, where the multitude of proteins comprises the target protein. The method further includes identifying, using the first binding site profile and the structure data, the target protein. The method further includes presenting the target protein to a user.

In general, in one aspect, embodiments relate to a system for identifying a target protein. The system includes a data repository storing structure data describing molecular properties of surfaces for a multitude of proteins. The system further includes a controlled server comprising a computer processor and a memory executable by the processor. The memory includes functionality for receiving a request to identify a target protein based on a ligand. The memory further includes functionality for identifying, using the ligand, a first protein, wherein the ligand binds with the first protein to form a ligand-protein complex. The memory further includes functionality for generating a first binding site profile for the first protein, where the first binding site profile describes molecular properties of the first protein. The memory further includes functionality for obtaining, from a controlled server, the structure data describing molecular properties of surfaces for a multitude of proteins, where the multitude of proteins comprises the target protein. The memory further includes functionality for identifying, using the first binding site profile and the structure data, the target protein. The memory further includes functionality for presenting the target protein to a user.

In general, in one aspect, embodiments relate to a non-transitory computer readable medium (CRM) storing various instructions for identifying a target protein. The instructions include functionality for receiving a request to identify a target protein based on a ligand. The instructions further include functionality for identifying, using the ligand, a first protein, where the ligand binds with the first protein to form a ligand-protein complex. The instructions further include functionality for generating a first binding site profile for the first protein, where the first binding site profile describes molecular properties of the first protein. The instructions further include functionality for obtaining, from a controlled server, structure data describing molecular properties of surfaces for a multitude of proteins, where the multitude of proteins comprises the target protein. The instructions further include functionality for identifying, using the first binding site profile and the structure data, the target protein. The instructions further include functionality for presenting the target protein to a user.

Other aspects of the invention will be apparent from the following description and the appended claims.

DETAILED DESCRIPTION

Figure 1:
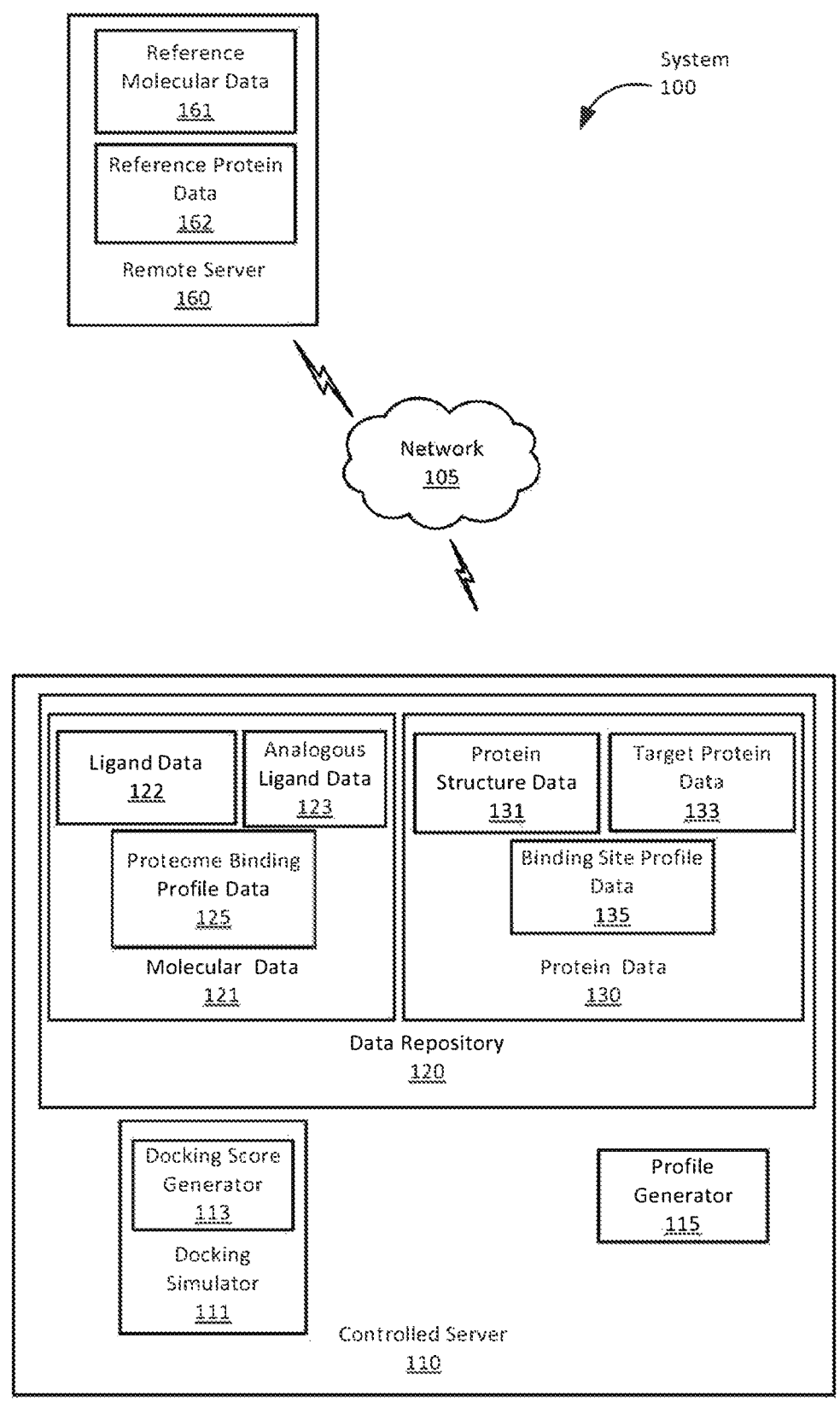
FIG. 1 shows a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

One or more embodiments of the invention include a method, a system, and a non-transitory computer readable medium for proteome docking to identify protein-ligand interactions. The invention may accept any molecule to identify interactions between the molecule and various protein structures. For example, embodiments of the invention may accept a molecule with a size up to 1000 daltons. One of ordinary skill in the art would appreciate molecules of other sizes may be permissible. In particular, one or more embodiments are directed to receiving a request to identify a target protein based on a ligand. Further, one or more embodiments are directed to identifying a first protein using the ligand. In one or more embodiments, the ligand binds with the first protein to form a ligand-protein complex. Additionally, one or more embodiments are directed to generating a first binding site profile for the first protein. In one or more embodiments, the first binding site profile describes molecular properties of the first protein. Further, one or more embodiments are directed to obtaining structure data describing molecular properties of surfaces for a plurality of proteins from a controlled server. In one or more embodiments, the plurality of proteins comprises the target protein. Furthermore, one or more embodiments are directed to identifying the target protein using the first binding site profile and the structure data. Additionally, one or more embodiments are directed to presenting the target protein to a user.

FIG. 1 shows a schematic diagram of a system in accordance with one or more embodiments of the invention. While FIG. 1 shows a configuration of components, other configurations may be used without departing from the scope of the invention. For example, various components may be combined to create a single component. As another example, the functionality performed by a single component may be performed by two or more components.

Turning to FIG. 1, in accordance with one or more embodiments of the invention, the system (100) may include one or more controlled servers (110). In one or more embodiments, the controlled server (110) includes various modules, such as a docking simulator (111), docking score generator (113), and a profile generator (115).

The controlled server (110) may store various data (e.g., molecular data (121), protein data (130)) in various data structures within a data repository (e.g., data repository (120)). In one or more embodiments of the invention, the data repository (120) is any type of storage unit and/or device (e.g., a file system, database, collection of tables, or any other storage mechanism) for storing data. Further, the data repository (120) may include multiple different storage units and/or devices. The multiple different storage units and/or devices may be of the same type or located at the same physical site.

In one or more embodiments, the controlled server (110) is operatively connected to a remote server (160) via a network (105). The remote server (160) may store various data (e.g., reference molecular data (161), reference protein data (162)) in various data structures within a data repository (not shown).

In one or more embodiments, the molecular data (121) includes ligand data (122). In general, a ligand may be an atom, a molecule, an ion, and/or a chemical compound which may bind to a protein. In one or more embodiments, a ligand is described as a drug, drug candidate, nutraceutical, vitamin, cofactor, and/or toxin. The ligand data (122) may include molecular properties of a ligand based on the molecular structure and/or chemical functionality of the ligand. Further, the ligand data (122) may include chemical properties, physical properties, and/or structural properties of a ligand. For example, the ligand data (122) may describe the biological activity and/or pharmacological activity of a test ligand in vivo and/or in vitro. In another example, the ligand data (122) may describe the effects a test ligand exhibits when chemically reacting with various inorganic and/or organic reagents. Further, the ligand data (122) may describe the manner in which a ligand interacts with UV-VIS and IR radiation. Furthermore, the ligand data (122) may include the nuclear magnetic resonance (NMR) spectra of a ligand, where the NMR spectroscopy determines the physical and chemical properties of one or more atoms of a ligand.

Further, the molecular data (121) includes molecular fingerprints of one or more molecules generated by the controlled server (110) in accordance with one or more embodiments. Molecular fingerprints may be a quantified value representing one or more molecular properties of a ligand. For example, the molecular properties of a test ligand may be converted into a string of binary digits and stored in a data repository as a molecular fingerprint, where each binary digit and/or sets of binary digits correspond to a particular molecular property of the test ligand. Further, the molecular fingerprint may represent the presence or absence of particular molecular substructures within the test ligand. In one or more embodiments, the molecular fingerprint describes molecular weight, molecular volume, molar refractivity, partition coefficients, permeability, bioavailability, number of atoms, type of atoms, number of bonds, length of bonds, number of rings, connectivity indices, solvent accessible surface areas, principal moment of inertia, partial charges, polarity indices, thermodynamic properties, and/or electrostatic surface descriptors.

Descriptors of one or more molecules may be stored in molecular data (121). Descriptors may be defined as numerical values that may characterize molecular properties of one or more molecules. In one or more embodiments, descriptors regarding one or more molecules are used to generate molecular fingerprints for one or more molecules. Descriptors may be used for molecular property calculations (QSPR—quantitative structure-property relationship) or chemical activity (QSAR—quantitative structure-activity relationship) calculations. In one or more embodiments, descriptors of molecules include 0D-descriptors (i.e., constitutional descriptors, count descriptors, bond counts, molecular weight, atom counts), 1D-descriptors (i.e., list of structural fragments, fingerprints, hydrogen-bond acceptor and/or donor), 2D-descriptors (i.e., graph invariants), 3D-descriptors (i.e., geometrical descriptors, surface properties, 3D-MoRSE descriptors, WHIM descriptors, GETAWAY descriptors, quantum-chemical descriptors, size, steric, surface and/or volume descriptors), and/or 4D-descriptors (i.e., derived from GRID and/or CoMFA methods, Volsurf).

In one or more embodiments, the molecular data (121) includes analogous ligand data (123). The analogous ligand data (123) may include molecular properties regarding one or more molecules that may be identified based on their similarity to a ligand stored in ligand data (122). For example, one or more analogous ligands may be identified by a computer processor (not shown) of a computing device (not shown) operatively connected to the controlled server (110), where the analogous ligands may be identified on the basis of molecular properties, biological properties, and/or chemical properties that are similar to the molecular properties of a test ligand stored in ligand data (122). In one or more embodiments, the analogous ligand data (123) describes the same type of molecular properties of analogous ligands as disclosed above regarding the properties of test ligands stored in ligand data (122).

In one or more embodiments, the molecular data (121) includes proteome binding profile data (125) for one or more proteome binding profiles. The proteome binding profile data (125) may include a proteome binding profile for one or more ligands. Further, a proteome binding profile may describe one or more proteins that interact with a molecule stored in ligand data (122) or analogous ligand data (123). For example, the proteome binding profile data (125) may include a proteome binding profile of a test ligand stored in the ligand data (122), where the proteome binding profile describes proteins that successfully bind with the test ligand to form a ligand-protein complex. In one or more embodiments, a ligand-protein complex is the resulting structure once a ligand successfully binds to a protein as a result of the ligand exhibiting affinity for one or more binding sites of the protein. In another example, a test ligand stored in ligand data (122) may undergo docking simulations with one or more proteins, and the resulting proteins that have a docking score satisfying a threshold may be inserted into the proteome binding profile of the test ligand. Further, a proteome binding profile may include a complete set of proteins, along with their binding affinities, that are predicted to interact and/or bind with a test ligand. In one or more embodiments, the molecular data (121) is determined experimentally during tangible and/or physical laboratory testing of molecules. In one or more embodiments, the molecular data (121) is obtained from reference molecular data (161) stored at a remote server (160). In one or more embodiments, the molecular data (121) includes data obtained from virtual docking simulations and/or computational binding predictions performed by the docking simulator (111) of one or more proteins with one or more ligands.

In one or more embodiments, the protein data (130) includes protein structure data (131). The protein structure data (131) may include molecular properties, such as geometric and/or biophysical properties, of one or more proteins. Further, the protein structure data (131) may include protein surface descriptors that describe molecular properties of one or more proteins, such as shape, planarity, geometry, electrostatic properties, amino acid residue composition, atomic composition, size, hydrophobicity, polarity, and/or flexibility. In one or more embodiments, the protein structure data (131) includes non-molecular attributes describing biological and/or biochemical activity of one or more proteins. In one or more embodiments, the protein structure data (131) is derived from experimentally-determined structures, protein structures derived from homology modeling, protein structure prediction, and/or ensembles of conformations of proteins. In one or more embodiments, the protein structure data (131) includes molecular properties of protein surfaces stored in binary digit and/or alphanumeric format to allow for matching and identification of other proteins exhibiting similar molecular properties.

In one or more embodiments, the protein data (130) includes target protein data (133). The target protein data (133) may include molecular properties of one or more proteins predicted to bind with a test ligand to form a ligand-protein complex. In one or more embodiments, a target protein is identified based on molecular similarity to other proteins that bind with molecules that are similar to a test ligand. For example, a target protein may be identified based on a similarity factor between the molecular properties of surfaces of the target protein and the molecular properties of a protein which binds with an analogous molecule. The similarity factor may be a threshold manually set by a user, or may be computed and set by a computing device.

In one or more embodiments, the protein data (130) includes binding site profile data (134) for one or more binding site profiles. The binding site profile data (134) may include a binding site profile for one or more proteins. In one or more embodiments, a binding site profile includes molecular properties that describe the chemical and geometric features of one or more binding sites of a protein. In one or more embodiments, a binding site profile of a protein includes binding affinities of one or more ligands for the protein. In one or more embodiments, the protein data (130) includes experimental data taken during tangible laboratory testing of proteins. In one or more embodiments, the protein data (130) includes data obtained from virtual docking simulations performed by the docking simulator (111) of one or more proteins with one or more ligands. In one or more embodiments, the protein data (130) is obtained from reference protein data (162) stored at a remote server (160). In one or more embodiments, the binding site profile data (135) includes molecular properties stored in binary digit and/or alphanumeric format to allow for matching with other proteins exhibiting similar molecular properties.

In one or more embodiments, the docking simulator (111) obtains and extracts molecular properties of a ligand from molecular data (121) and molecular properties of a protein from protein data (130) in order to simulate binding between the ligand and one or more binding sites of the protein. Further, docking may be described as a computational simulation of a ligand binding to one or more binding sites of a protein. Further, docking simulations may be described as predicting, reproducing, and/or synthesizing the resulting structure of the ligand-protein complex after a ligand binds with a binding site of a protein. In one or more embodiments, the docking score generator (113) creates a docking score for each ligand and protein pair, where the docking score directly correlates with the degree of compatibility between a ligand and one or more binding sites of a protein, and/or the degree of stability of the resulting ligand-protein complex. Further, the docking score may correlate with the number of favorable intermolecular interactions increasing the stability of the ligand-protein complex, such as hydrogen bonding, metal coordination, hydrophobic forces, van der Waals forces, $\pi$-$\pi$ interactions, halogen bonding, electrostatic and/or electromagnetic effects. Docking score confidence may be calculated by comparing predicted protein-ligand complex docking scores with scores obtained by docking the same ligand to randomly-selected proteins. In one or more embodiments, docking simulation and docking score generation may be applied with statistical analysis in order to extrapolate and predict the interaction between a ligand and a binding site of a protein. The docking simulator (111) may execute one or more docking simulation algorithms, for example, GOLD, FlexX, TarFisDock, TarSearch-X, and/or TarSearch-M. One of ordinary skill in the art would appreciate other docking simulation algorithms may be compatible with and executed by the docking simulator (111).

In one or more embodiments, the profile generator (115) produces one or more proteome binding profiles that are stored in proteome binding profile data (125). For example, the profile generator (115) may obtain and extract protein data (130) regarding one or more proteins that bind with a test ligand in order to generate a proteome binding profile for the test ligand. In one or more embodiments, the profile generator (115) produces one or more binding site profiles that are stored in binding site profile data (134). For example, the profile generator (115) may obtain and extract protein data (130) and/or molecular data (121) in order to generate a binding site profile describing molecular properties of one or more binding sites of a target protein, as well as describing the molecular properties of ligands that successfully bind to the one or more binding sites of the target protein.

The system (100) may include one or more computing devices. The computing device may take the form of a specialized computer system. The computing device may be implemented on the same or different specialized computer systems of the type found and described in relation to FIG. 5. In one or more embodiments, the computing device may be a combination of hardware and software configured to display data using a display device. For example, the computing device may be a mobile phone, a desktop computer, a laptop computer, a tablet computer, or any other device configured to operate as described herein.

Figure 2:
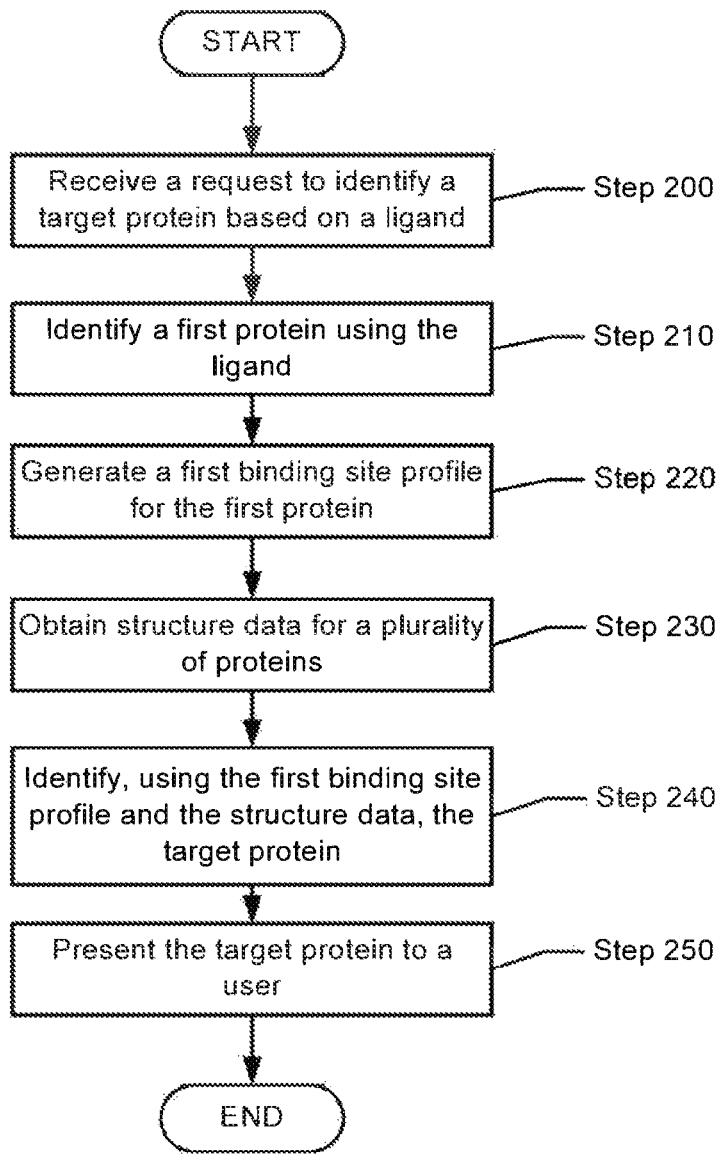
FIGS. 2, 3A, and 3B show flowcharts in accordance with one or more embodiments of the invention.
Figure 3A:
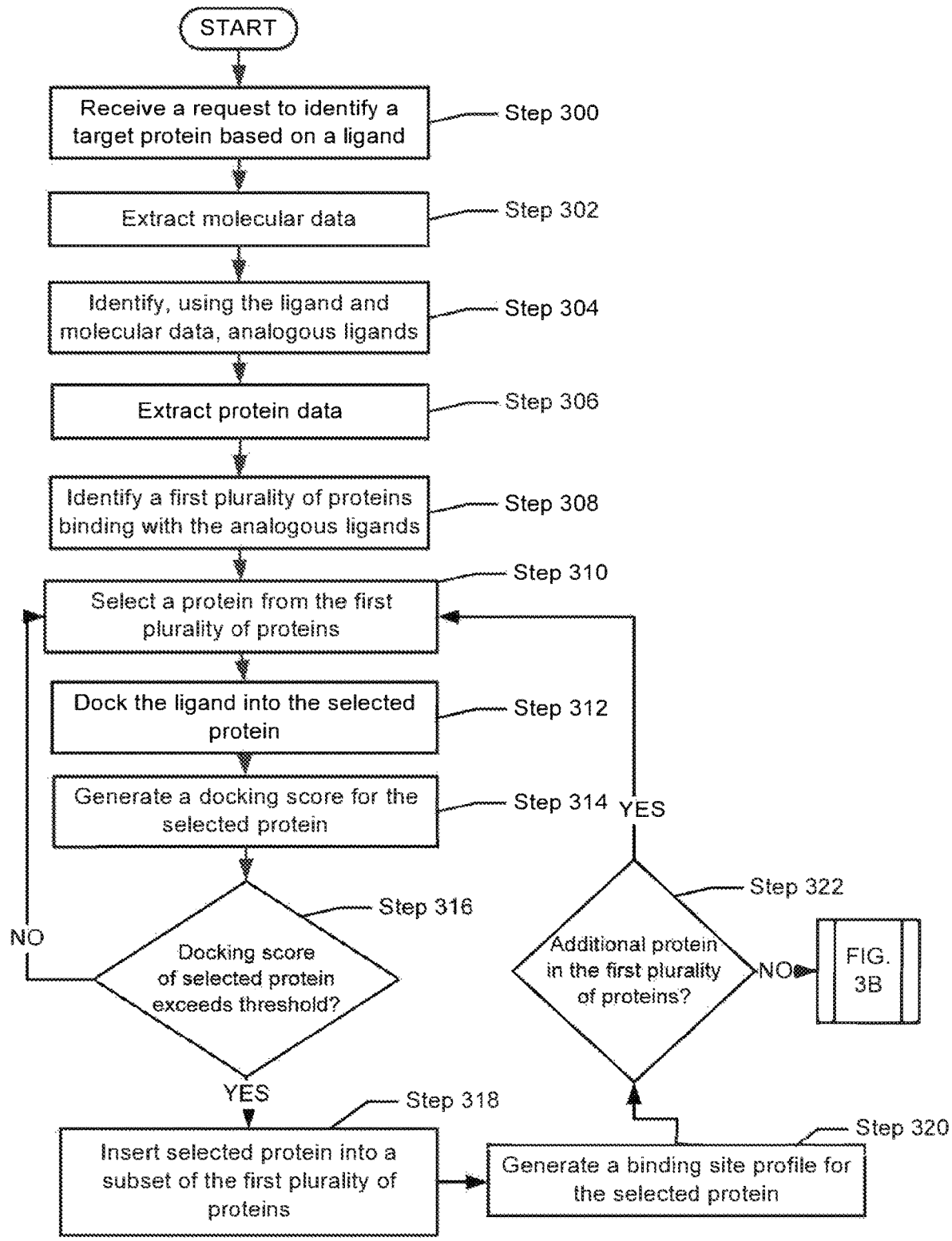
Figure 3B:
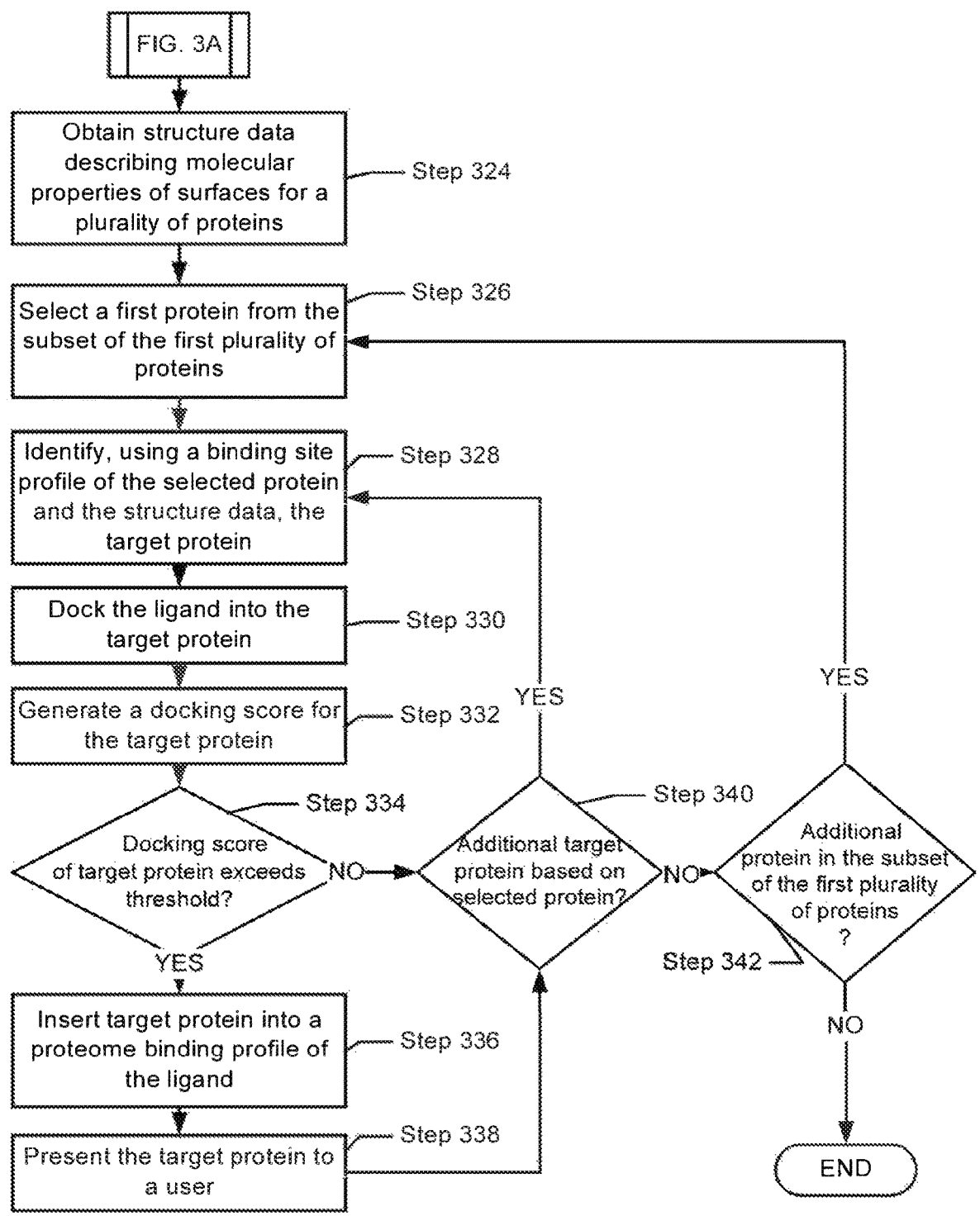

FIGS. 2, 3A, and 3B show flowcharts in accordance with one or more embodiments of the invention. While the various steps in these flowcharts are presented and described sequentially, one of ordinary skill in the art will appreciate that some or all of the steps may be executed in different orders, may be combined or omitted, and some or all of the steps may be executed in parallel. Furthermore, the steps may be performed actively or passively. By way of an example, determination steps may not require a computer processor to process an instruction unless an interrupt is received to signify that condition exists in accordance with one or more embodiments of the invention.

FIG. 2 shows a flowchart describing a method for identifying a target protein in accordance with one or more embodiments of the invention. In Step 200, one or more embodiments are directed to receiving a request to identify a target protein based on a ligand. In one or more embodiments, the ligand received in Step 200 is also referred to as a test ligand. In one or more embodiments, in response to the request received in Step 200, a first protein is identified in Step 210 by a computing device, where the test ligand binds with the first protein to form a ligand-protein complex. The first protein may be identified as described by Step 300-Step 322 of FIG. 3A.

In Step 220, the computing device generates a binding site profile for the first protein in accordance with one or more embodiments. The binding site profile may describe the molecular properties and geometric features of one or more binding sites of the first protein.

In Step 230, in accordance with one or more embodiments, the computing device extracts protein structure data describing molecular properties of surfaces of one or more proteins. In one or more embodiments, the protein structure data is obtained from a private database hosted by a controlled server.

In Step 240, a target protein is identified using the binding site profile of the first protein and the protein structure data in accordance with one or more embodiments. A determination may be made whether the binding site of the first protein satisfies a similarity threshold with molecular properties of surfaces of one or more proteins within the protein structure data. Further, if a protein is identified from the protein structure data that exhibits molecular properties matching the molecular properties within the binding site profile of the first protein, then the matching protein identified from the protein structure data may be labeled as a target protein.

In Step 250, the target protein is transmitted to one or more computing devices for presentation to a user in accordance with one or more embodiments. In one or more embodiments, for example, the target protein and test ligand are transmitted to a computing device for display on the respective computing device. The various molecular properties associated with the target protein and/or test ligand may also be transmitted for display on the computing device.

FIGS. 3A and 3B show a flowchart describing a method for identifying a target protein in accordance with one or more embodiments of the invention. In Step 300, one or more embodiments are directed to receiving a request to identify a target protein based on a ligand. Further, in response to the request, a computing device may identify molecular properties of the ligand. For example, chemical properties, physical properties, structural properties, pharmacological properties, and/or biological properties of the test ligand may be identified. Next, based on the molecular properties of the test ligand, a molecular fingerprint of the test ligand may be generated. For example, the molecular properties of the test ligand may be converted into a string of binary digits and stored in a data repository as a molecular fingerprint of the test ligand.

In Step 302, in accordance with one or more embodiments and in response to the request received in Step 300, the computing device obtains and extracts molecular data including molecular properties of one or more molecules. In one or more embodiments, the molecular data is obtained from a publicly-accessible reference molecular database providing chemical and structural properties of one or more molecules. In one or more embodiments, the molecular data is obtained from a private database hosted by a controlled server.

In Step 304, in accordance with one or more embodiments and in response to the molecular data extracted in Step 302, molecular fingerprints of one or more molecules from the molecular data are extracted. In one or more embodiments, molecular fingerprints of one or more molecules using the molecular data extracted in Step 302 are generated. Further, one or more molecules that are structurally and/or molecularly analogous to the test ligand are identified based on their molecular fingerprints. For example, a computer processor of the computing device may identify one or more molecules that have an analogous molecular fingerprint as the molecular fingerprint of the test ligand generated in Step 300. Said in another way, a computer processor may identify one or more molecules having molecular fingerprints that overlap with the molecular fingerprint of the test ligand. Furthermore, one or more molecules that possess molecular fingerprints similar to the molecular fingerprint of the test ligand may be labeled as analogous ligands by the computer processor. For example, a molecule that has a molecular fingerprint satisfying a similarity threshold when compared with the molecular fingerprint of a test ligand may be labeled as an analogous ligand by the computer processor.

In Step 306, in accordance with one or more embodiments and in response to identifying the analogous ligands in Step 304, the computing device obtains and extracts protein data including molecular properties of one or more proteins. In one or more embodiments, the protein data is obtained from a publicly-accessible reference protein database providing chemical and structural properties of one or more proteins. In one or more embodiments, the protein data is obtained from a private database hosted by a controlled server.

In Step 308, in accordance with one or more embodiments and in response to extracting the protein data in Step 306, the protein data and molecular data is used to identify a first plurality of proteins that bind with the analogous ligands. For example, a computer processor may use the molecular properties of a particular analogous ligand to identify one or more proteins that interact with that particular analogous ligand to form a ligand-protein complex.

In Step 310, in accordance with one or more embodiments and in response to identifying the first plurality of proteins that bind with the analogous ligands in Step 306, a specific protein is selected from the first plurality of proteins. For example, proteins are iteratively selected from the first plurality of proteins by the computing device, and subsequently, the test ligand is docked into the selected protein in the ensuing steps.

In Step 312, in accordance with one or more embodiments and in response to selecting a protein from the first plurality of proteins, a docking simulation is performed with the selected protein and the test ligand. Here, molecular properties of the selected protein and molecular properties of the test ligand may be extracted to simulate an interaction between the selected protein and the test ligand. For example, a computer processor may perform computations using a molecular fingerprint of a test ligand and molecular properties of a selected protein in order to simulate binding between the test ligand and a binding site of the selected protein. In one or more embodiments, the computer processor docks the test ligand into one or more binding sites of the selected protein.

In Step 314, in accordance with one or more embodiments and in response to performing a docking simulation, a docking score is generated for the selected protein. The docking score may correlate with the degree of compatibility between the test ligand and one or more binding sites of the selected protein. For example, a high docking score may indicate a high affinity of the test ligand for a binding site of the selected protein.

In Step 316, in response to generating a docking score for the selected protein, a determination whether the docking score of the selected protein meets and/or exceeds a docking score threshold is made using the computing device in accordance with one or more embodiments. The docking score threshold may be manually set by a user, or may be computed and set by a computer processor. If the docking score satisfies the docking score threshold, then the process proceeds to Step 318. If the docking score does not satisfy the docking score threshold, then the process proceeds to Step 310 to iteratively select the next protein in the first plurality of proteins.

In Step 318, in response to determining that the docking score of the selected protein satisfies the docking score threshold, the selected protein is inserted into a subset of the first plurality of proteins in accordance with one or more embodiments. For example, if a selected protein satisfies the docking score threshold, then the selected protein may be inserted into a subgroup for further processing in ensuing steps. If a selected protein does not satisfy the docking score threshold, then the selected protein may be deemed incompatible with the test ligand and the process may return to Step 310 to iteratively select a different protein.

In Step 320, in response to inserting the selected protein into the subset of the first plurality of proteins, a binding site profile for the selected protein is generated in accordance with one or more embodiments. The binding site profile may describe the molecular properties and geometric features of one or more binding sites of the selected protein. In one or more embodiments, the binding site profile of the selected protein includes binding affinities of one or more ligands for one or more binding sites of the selected protein. Further, the binding site profile of a selected protein may describe the particular molecular properties and/or molecular fingerprints that may result in a potential ligand having a high affinity for one or more binding sites of a selected protein.

In Step 322, a determination is made using the computing device whether additional proteins remain in the first plurality of proteins in accordance with one or more embodiments. For example, a computer processor may determine whether additional proteins remain to be selected in the first plurality of proteins for docking simulations. If no additional proteins are detected, then the process proceeds to Step 324. If an additional protein is detected, then the process proceeds to Step 310 to iteratively select the next protein in the first plurality of proteins.

In Step 324, in accordance with one or more embodiments, the computing device extracts protein structure data describing molecular properties of surfaces of one or more proteins. In Step 326, a specific protein is selected from the subset of the first plurality of proteins in accordance with one or more embodiments. For example, proteins are iteratively selected from the subset of the first plurality of proteins using the computing device. In addition, the binding site profile of the selected protein may also be extracted using the computing device.

In Step 328, a target protein is identified using the binding site profile of the selected protein and the protein structure data in accordance with one or more embodiments. A determination is then made whether the binding site of the selected protein satisfies a similarity threshold with molecular properties of one or more proteins within the protein structure data. If a protein is identified from within the protein structure data that exhibits molecular properties matching the binding site profile of the selected protein, then the protein identified from the protein structure data may be identified as a target protein. Matching surfaces of one or more proteins by amino acid sequence may be clustered, and matching surfaces may be ranked according to similarity of molecular properties.

In one or more embodiments, matching is performed on the basis of the molecular properties of the surface of one or more proteins, such as geometric and electrostatic features of protein surfaces, while accounting for ligand and/or binding site flexibility. Flexibility may refer to the algorithm simulating one or more positions and/or conformations of the ligand and/or of the binding site of a protein. For example, docking simulations may be performed with manipulations along the translational, rotational, and/or torsional planes of a ligand. Further, docking simulations may be performed with various conformations of a ligand, such as rotations along a single bond, to determine the optimal orientation of the ligand for binding one or more binding sites of a protein. Similarly, docking simulations may be performed with various adjustments of the structure of the binding site of a protein in order to achieve a conformation and/or orientation between protein and ligand such that the Gibbs free energy of the ligand-protein interaction is minimized. Furthermore, the relative orientation of a ligand and binding site of a protein may affect the type of signal produced, and therefore, docking simulations may predict the binding affinity of a ligand for a binding site of a protein, as well as the type of signal produced upon formation of a ligand-protein complex.

In Step 330, in accordance with one or more embodiments and in response to identifying a target protein from the protein structure data, a docking simulation is performed with the target protein and the test ligand. Here, molecular properties of the target protein and molecular properties of the test ligand may be extracted to simulate an interaction between the target protein and the test ligand. For example, a computer processor may perform computations using a molecular fingerprint of a test ligand and molecular properties and/or protein structure data of a target protein in order to simulate binding between the test ligand and a binding site of the target protein. In one or more embodiments, the computer processor docks the test ligand into one or more binding sites of the target protein. The test ligand may be docked directly to the highest matching surfaces based on docking score, which may be limited to a local area surrounding the matching surfaces of the target protein.

In Step 332, in accordance with one or more embodiments and in response to performing a docking simulation, a docking score for the target protein is generated. The docking score may correlate with the degree of compatibility between the test ligand and one or more binding sites of the target protein. For example, a high docking score may indicate a high affinity of the test ligand for a binding site of the target protein.

In Step 334, in response to generating a docking score for the target protein, a determination is made whether the docking score of the target protein meets and/or exceeds a docking score threshold in accordance with one or more embodiments. If the docking score satisfies the docking score threshold, then the process proceeds to Step 336. If the docking score does not satisfy the docking score threshold, then the process proceeds to Step 340.

In Step 336, in response to determining that the docking score of the target protein satisfies the docking score threshold, the target protein is inserted into a proteome binding profile of the test ligand in accordance with one or more embodiments. The proteome binding profile of the test ligand may include one or more proteins that are predicted and/or have been experimentally determined to bind with the test ligand. For example, if a target protein satisfies the docking score threshold, then the target protein may be inserted into a proteome binding profile of the test ligand. If a target protein does not satisfy the docking score threshold, then the structure of the selected protein may be deemed incompatible with the test ligand and the process may proceed to Step 340. Additional molecules similar to a test ligand may be included in the docking simulation step to directly compare the proteome binding profiles of molecularly related compounds. Proteome binding profiles may be used to cluster different molecules and their respective predicted protein binding sites. By generating lists of predicted protein interactions, the method described herein may bridge molecules that share first-degree protein interactions.

In Step 338, the target protein is transmitted to one or more computing devices for presentation to a user in accordance with one or more embodiments. In one or more embodiments, for example, the target protein and test ligand are transmitted to a computing device for display on the respective computing device. Various molecular properties associated with the target protein and/or test ligand may also be transmitted for display on the computing device.

In Step 340, a determination is made whether additional target proteins remain based on the selected protein in accordance with one or more embodiments. For example, a computer processor of the computing device may determine whether additional target proteins are identified in Step 328 based on the molecular properties of the protein selected in Step 326. If no additional target proteins are detected, then the process proceeds to Step 342. If an additional target protein is detected, then the process proceeds to Step 330 for the computer processor to iteratively select the next target protein, and to perform docking simulations with the next target protein with the test ligand.

In Step 342, a determination is made by the computing device whether additional proteins remain in the subset of the first plurality of proteins in accordance with one or more embodiments. For example, a computer processor of the computing device may determine whether additional proteins remain to be selected in the subset of the first plurality of proteins in order to identify target proteins for docking simulations. If no additional proteins are detected, then the process ends. If an additional protein is detected, then the process proceeds to Step 326 to iteratively select the next protein in the subset of the first plurality of proteins.

In one or more embodiments, the controlled server includes protein data describing functionality of one or more proteins. For example, the protein data hosted by the controlled server may describe biological roles and/or biological pathways associated with one or more proteins. In another example, the protein data may describe one or more diseases and/or treatments that are correlated with the activity of one or more proteins. Therefore, the test ligand may be predicted to promote and/or inhibit the biological role associated with the target protein identified in Step 336. Further, the mechanism of action of a test ligand may be determined based on the identification of the particular proteins predicted to be targeted by the test ligand. For example, if a drug that is used for treatment of a first disease is predicted to interact with a particular protein implicated with a second disease, then the drug may be repurposed for treatment of the second disease. That is, the method described herein may allow for the identification of new uses for existing compounds. Further, the method described herein may allow for the identification of additional target proteins of a drug. For example, a single target protein for a drug may be identified, but the drug may have the potential for interacting with additional proteins. Therefore, the method described herein may predict a potential interaction between the drug and additional proteins. Additionally, based on the biological role of the additional proteins, the potential beneficial effects, adverse effects, and/or toxicity of the drug may be predicted.

Predictions of protein binding interactions may permit the incorporation of publicly-available reference databases, including drug-target associations, gene-disease associations, protein-protein interactions, and pathway analysis. Protein-protein interactions (PPIs) may occur when two or more proteins physically associate to carry out cellular functions. Ligand binding to a given protein may also influence the activity of surrounding proteins. Incorporation of the method described herein with a database of PPI interactions may allow for identification of second-degree protein interactions. Additionally, pathway analysis may allow for identification of biological processes of various proteins. Further, target proteins may be cross-referenced with a database of drug-target associations to identify potential synergistic or antagonistic drug-drug interactions. Furthermore, target proteins may also be cross-referenced with a database of gene-disease associations to reveal new possibilities for therapeutic applications or combination drug therapies with a test ligand.

FIGS. 4A, 4B, 4C, 4D, and 4E show an example for identifying a target protein in accordance with one or more embodiments of the invention. The following example is for explanatory purposes only and not intended to limit the scope of the invention. For the purposes of the example only, consider the scenario in which a drug candidate (401) is received as a test ligand by a controlled server or other computing device (not shown). In this example, the controlled server or other computing device includes (or has access to) a data repository (410) storing data regarding molecular properties of the drug candidate (401), one or more ligands (e.g., analogous molecule A (403A), analogous molecule B (403B)) that are molecularly similar to the drug candidate (401), and one or more proteins (e.g., compatible protein A (405A), compatible protein β (405B), compatible protein C (405C), compatible protein D (405D)) capable of binding with the drug candidate and/or one or more analogous molecules. Further, the data repository (410) includes protein structure data (411) describing molecular properties, such as geometric and/or biophysical properties, of surfaces of one or more proteins (e.g., protein α (412A), protein β (412B), protein N (412N)). In this example, the controlled server is operatively connected to one or more remote servers (not shown) storing reference molecular data of one or more molecules and/or proteins.

Figure 4A:
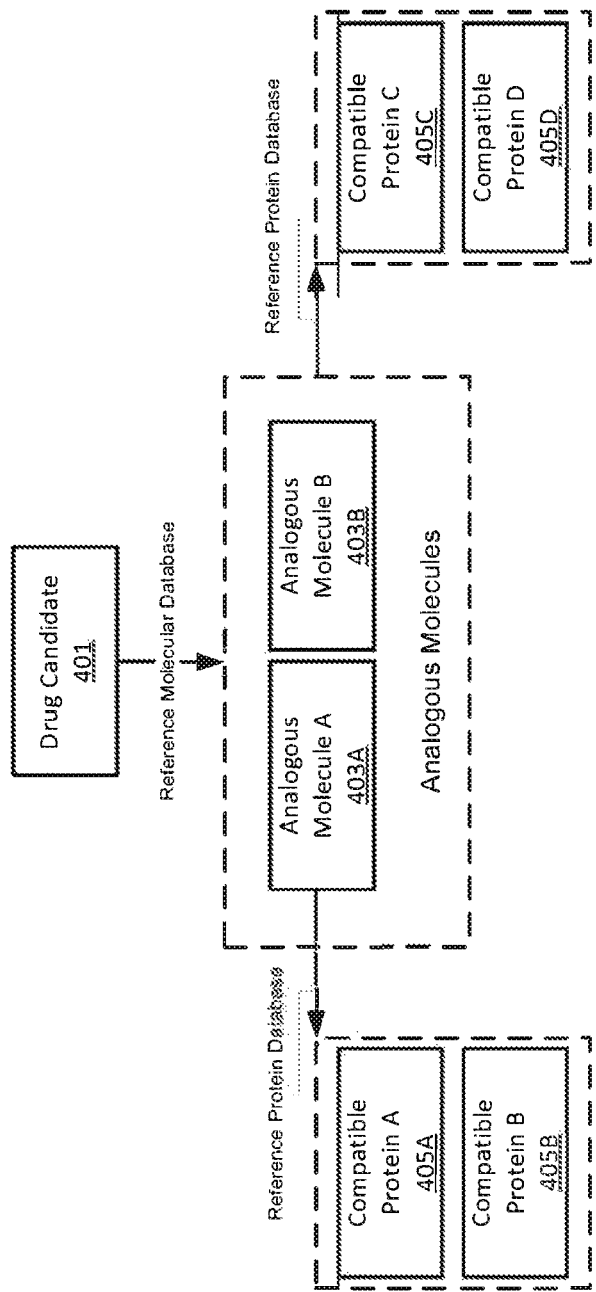
FIGS. 4A, 4B, 4C, 4D, and 4E show an example in accordance with one or more embodiments of the invention.

Turning to FIG. 4A, the controlled server (or any computing device using a processor of some sort) generates a molecular fingerprint based on the molecular properties of the drug candidate (401), and stores the molecular fingerprint in the data repository (410). The molecular properties used for generating the molecular fingerprint may be determined through direct laboratory testing of the drug candidate (401). Additionally, the molecular properties may be obtained from a reference molecular database.

Next, a reference molecular database is accessed to obtain reference molecular data regarding one or more molecules. One or more molecular fingerprints may be generated for various molecules using the reference molecular data for storage in the data repository (410). Here, the molecular fingerprint of the drug candidate (401) and the reference molecular data are used to identify one or more analogous molecules (e.g., analogous molecule A (403A), analogous molecule B (403B)), where the molecular fingerprint of the drug candidate and the molecular fingerprint of the analogous molecules satisfy a similarity threshold.

Once the analogous molecules are identified, a reference protein database is accessed to obtain reference protein data regarding one or more proteins. The reference protein data and reference molecular data are then used to identify one or more proteins (e.g., compatible protein A (405A), compatible protein B (405B), compatible protein C (405C), compatible protein D (405D)) that bind with the analogous molecules.

Figure 4B:
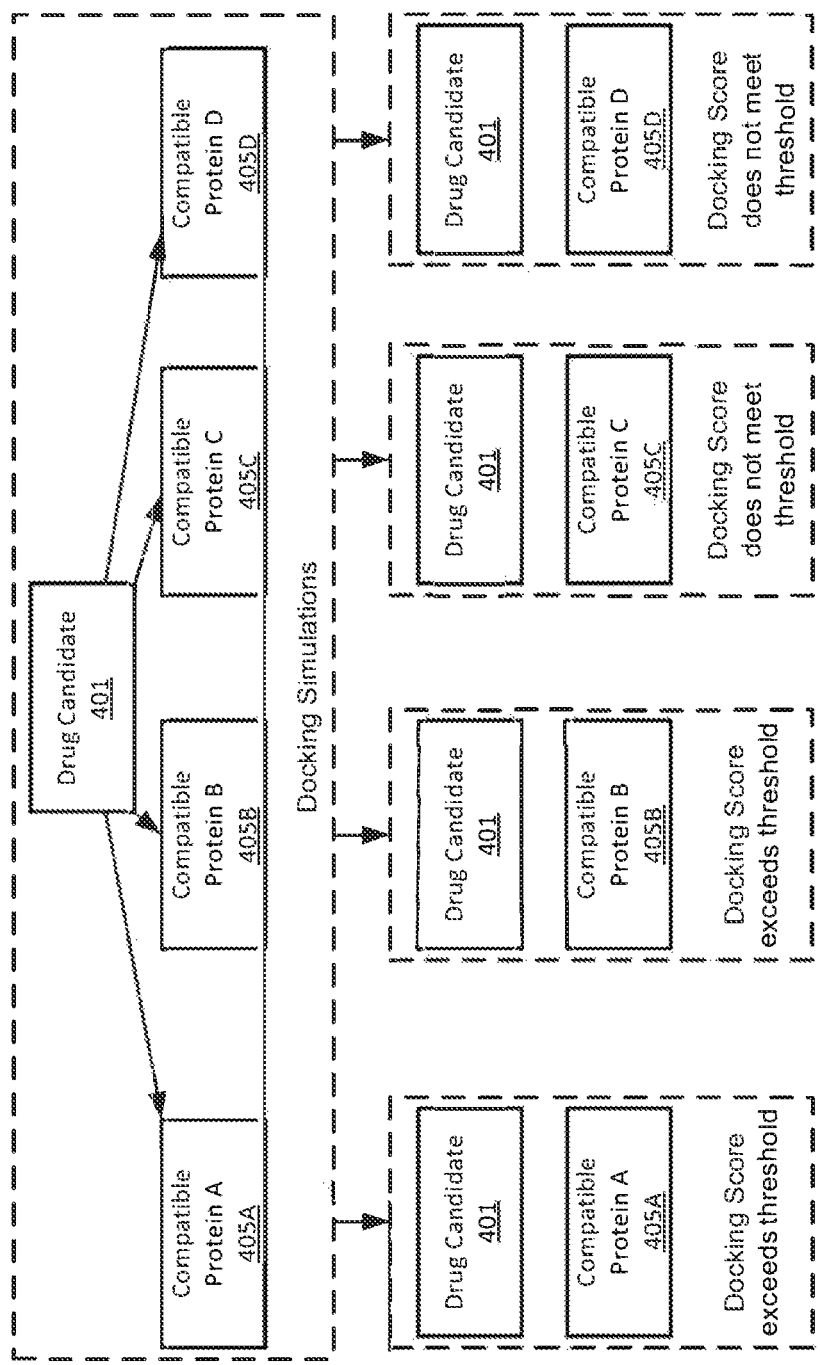
Figure 4C:
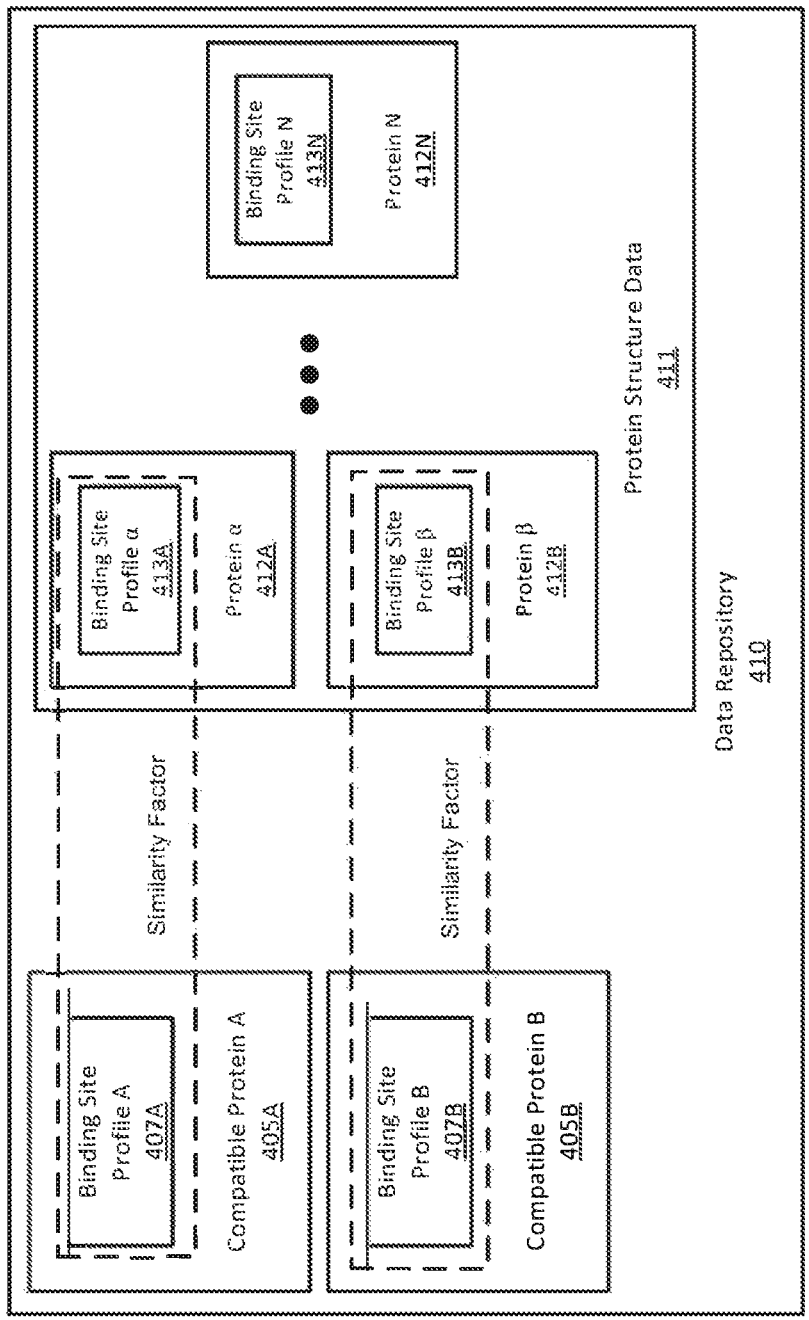

Next, a specific protein is selected from the compatible proteins for docking simulations. For example, proteins are iteratively selected from the list of compatible proteins by the computing device, and subsequently, the drug candidate is docked into the selected protein. Here, the molecular properties of the selected protein and molecular properties of the drug candidate are extracted to simulate an interaction between the selected protein and the drug candidate. In response to performing a docking simulation, a docking score is generated for the selected protein. As shown in FIG. 4B, the docking simulation between the drug candidate (401) and compatible protein A (405A) results in a docking score exceeding a docking score threshold. In addition, the docking simulation between the drug candidate (401) and compatible protein B (405B) results in a docking score exceeding a docking score threshold. However, in this example, the docking simulation between the drug candidate (401) and compatible protein C (405C), and between the drug candidate and compatible protein D (405D), do not satisfy the docking score threshold. Therefore, a binding site profile for compatible protein A (e.g., binding site profile A (407A)) and for compatible protein B (e.g., binding site profile B (407B)) is generated.

Further, the computing device extracts protein structure data describing molecular properties of surfaces of one or more proteins. Then one or more proteins (e.g., protein α (412A), protein β (412B)) are identified using the binding site profile of the compatible proteins (e.g., binding site profile A (407A), binding site profile B (407B)) and the protein structure data (e.g., binding site profile α (413A), binding site profile β (413B)). In this example, a determination is made whether the binding site profiles of the compatible proteins (e.g., binding site profile A (407A), binding site profile B (407B)) satisfy a similarity threshold with molecular properties of one or more proteins within the protein structure data (e.g., binding site profile α (413A), binding site profile β (413B), binding site profile N (413N)).

The resulting proteins that are identified and are labeled as interaction candidates proteins (e.g., protein α (412A), protein β (412B)).

Figure 4D:
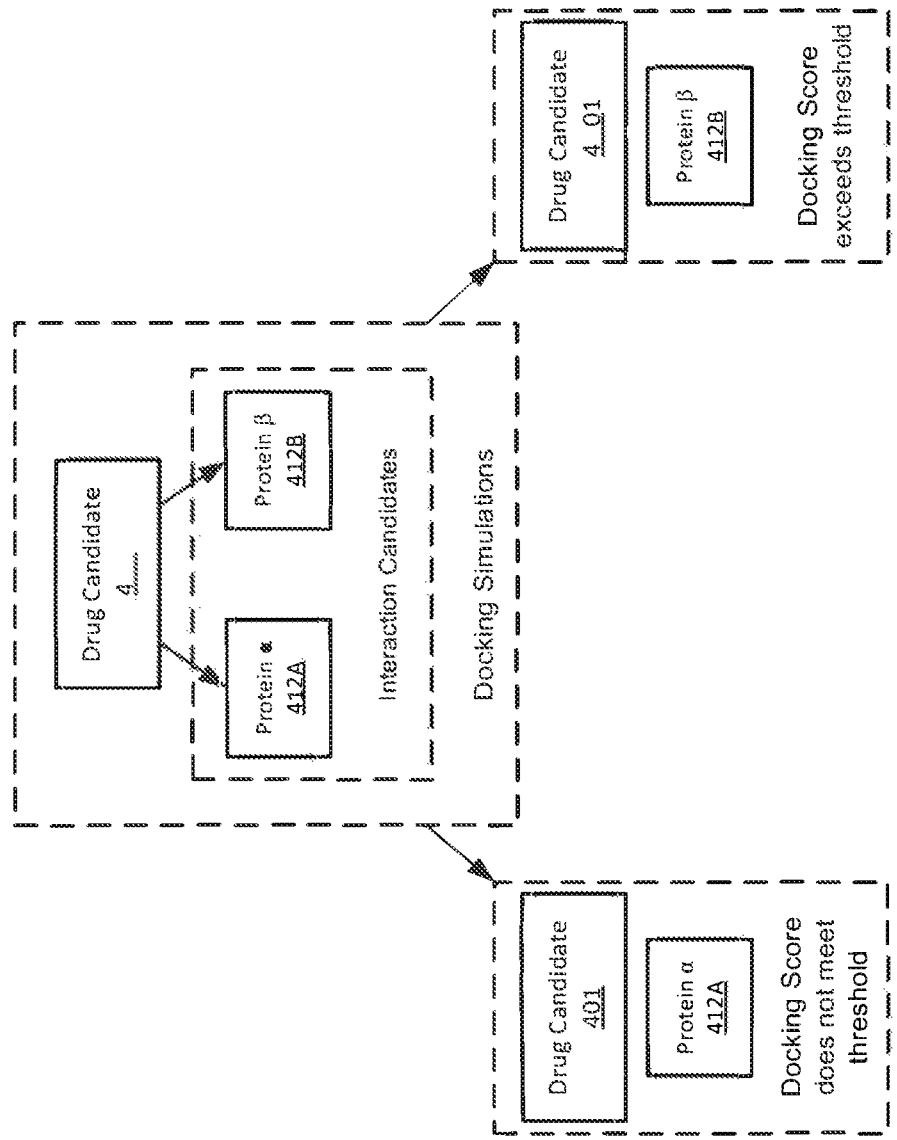
Figure 4E:
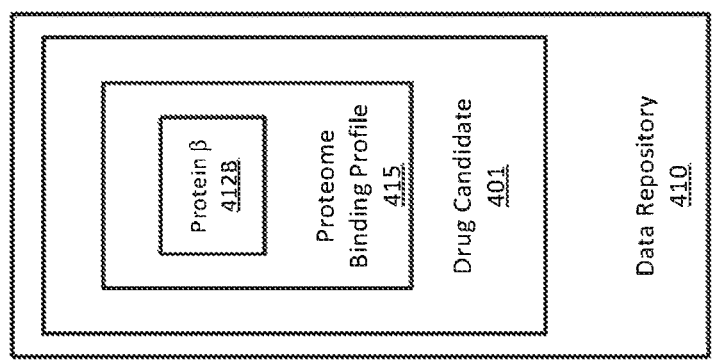

Furthermore, a docking simulation is performed with the interaction candidates and the drug candidate. Here, molecular properties of the drug candidate and molecular properties of the interaction candidates are extracted to simulate an interaction between the interaction candidates and the drug candidate. As shown in FIG. 4D, the docking simulation between the drug candidate (401) and interaction candidate protein β (412B) results in a docking score exceeding a docking score threshold. However, in this example, the docking simulation between the drug candidate (401) and interaction candidate protein α (412A) does not satisfy the docking score threshold. Therefore, as shown in FIG. 4E, a proteome binding profile (415) is generated for the drug candidate (401), which includes protein β (412B).

Figure 5:
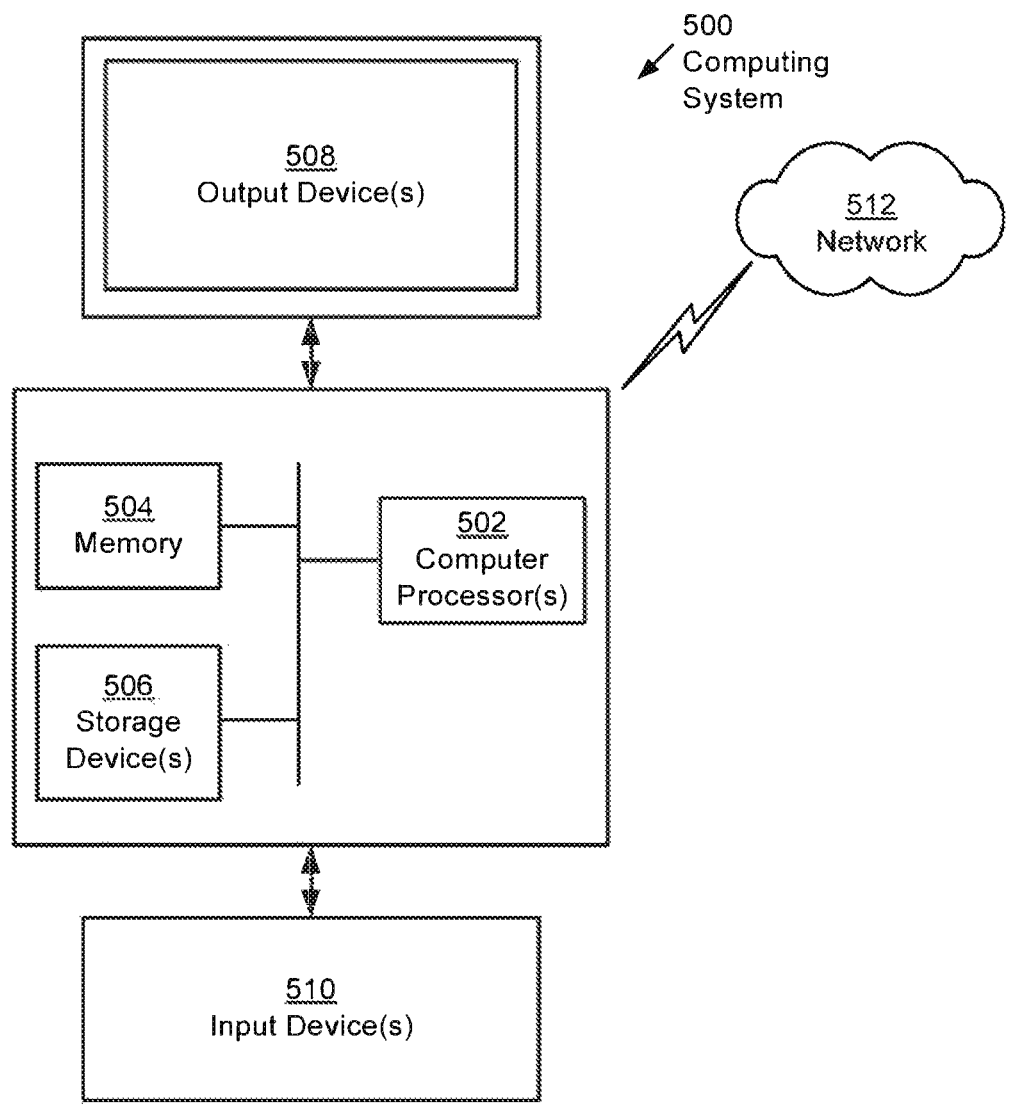
FIG. 5 shows a computing system in accordance with one or more embodiments of the invention.

Embodiments of the invention may be implemented on a computing system. Any combination of mobile, desktop, server, embedded, or other types of hardware may be used. For example, as shown in FIG. 5, the computing system (500) may include one or more computer processor(s) (502), associated memory (504) (e.g., random access memory (RAM), cache memory, flash memory, etc.), one or more storage device(s) (506) (e.g., a hard disk, an optical drive such as a compact disk (CD) drive or digital versatile disk (DVD) drive, a flash memory stick, etc.), and numerous other elements and functionalities. The computer processor(s) (502) may be an integrated circuit for processing instructions. For example, the computer processor(s) may be one or more cores, or micro-cores of a processor. The computing system (500) may also include one or more input device(s) (510), such as a touchscreen, keyboard, mouse, microphone, touchpad, electronic pen, or any other type of input device. Further, the computing system (500) may include one or more output device(s) (508), such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system (500) may be connected to a network (512) (e.g., a local area network (LAN), a wide area network (WAN) such as the Internet, mobile network, or any other type of network) via a network interface connection (not shown). The input and output device(s) may be locally or remotely (e.g., via the network (512)) connected to the computer processor(s) (502), memory (504), and storage device(s) (506). Many different types of computing systems exist, and the aforementioned input and output device(s) may take other forms.

Software instructions in the form of computer readable program code to perform embodiments of the invention may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a computer processor(s), is configured to perform embodiments of the invention.

Further, one or more elements of the aforementioned computing system (500) may be located at a remote location and connected to the other elements over a network (512). Further, embodiments of the invention may be implemented on a distributed system having a plurality of nodes, where each portion of the invention may be located on a different node within the distributed system. In one embodiment of the invention, the node corresponds to a distinct computing device. Alternatively, the node may correspond to a computer processor with associated physical memory. The node may alternatively correspond to a computer processor or micro-core of a computer processor with shared memory and/or resources.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method comprising:
   receiving, from a computing device, a request to identify a target protein based on a test ligand;
   identifying, using the test ligand and a plurality of docking simulations, a plurality of test-ligand-and-analogous-ligand binding proteins, wherein the plurality of test-ligand-and-analogous-ligand binding proteins are capable of binding with the test ligand and one or more analogous ligands, by:
      extracting, from a reference molecular database, molecular data comprising molecular properties of a plurality of ligands;
      identifying analogous ligands for the test ligand from the plurality of ligands by comparing the test ligand and the molecular properties of the plurality of ligands;
      extracting, from a reference protein database, protein data for a plurality of proteins;
      identifying a plurality of analogous-ligand protein complexes by comparing protein data for the plurality of proteins and the analogous ligands, wherein the plurality of analogous-ligand protein complexes comprise a subset of analogous binding proteins from the plurality of proteins, wherein the subset of analogous binding proteins are capable of binding with the analogous ligands; and
      performing the plurality of docking simulations using the test ligand and the subset of analogous binding proteins to identify the plurality of test-ligand-and-analogous-ligand binding proteins wherein performing the plurality of docking simulations further comprises:
         simulating docking of the test ligand into the subset of analogous binding proteins to generate docking scores for the subset of analogous binding proteins; and
         comparing the docking scores for the subset of analogous binding proteins to a first pre-determined threshold;
   generating binding site profiles for the plurality of test-ligand-and-analogous-ligand binding proteins, wherein the binding site profiles comprise molecular properties of the plurality of test-ligand-and-analogous-ligand binding proteins;
   obtaining, from a server device, structure data comprising molecular properties of surfaces for proteins;
   comparing the binding site profiles for the plurality of test-ligand-and-analogous-ligand binding proteins with the structure data to identify one or more candidate proteins;
   performing a docking simulation using the test ligand and the one or more candidate proteins, wherein performing the docking simulation comprises:
      simulating docking of the test ligand into one or more binding sites of the one or more candidate proteins to generate one or more docking scores for the one or more candidate proteins; and
      identifying the target protein from the one or more candidate proteins by comparing the one or more docking scores of the one or more candidate proteins to a second pre-determined threshold;
   inserting the target protein into a proteome binding profile of the test ligand;
   providing, for display, to one or more client devices, the target protein; and
   generating, based on the proteome binding profile of the test ligand, a therapeutic treatment utilizing the test ligand.

2. The method of claim 1,
   wherein the target protein comprises a plurality of target binding sites, and
   wherein the structure data further describes molecular properties of the plurality of target binding sites.

3. The method of claim 2, wherein identifying the target protein further comprises:
   identifying, using the binding site profiles for the plurality of test-ligand-and-analogous-ligand binding proteins and the structure data, a target binding site of the plurality of target binding sites; and
   providing, for display, to the one or more client devices, the target binding site.

4. The method of claim 1, wherein identifying the one or more candidate proteins further comprises:
   generating a similarity measure by comparing the binding site profiles of the plurality of test-ligand-and-analogous-ligand binding proteins to the structure data, and
   determining that the similarity measure exceeds a third pre-determined threshold.

5. The method of claim 1, wherein each protein of the subset of analogous binding proteins comprises a plurality of binding sites.

6. The method of claim 5, wherein performing the plurality of docking simulations further comprises simulating docking of the test ligand with regard to the plurality of binding sites.

7. The method of claim 1, wherein identifying the analogous ligands comprises:
   identifying molecular properties of the test ligand;
   generating a molecular fingerprint based on the molecular properties of the test ligand;
   using the molecular data, generating molecular fingerprints of each ligand of the plurality of ligands; and
   identifying the analogous ligands based on similarity between the molecular fingerprints of the plurality of ligands and the molecular fingerprint of the test ligand.

8. A system comprising:
   a data repository storing structure data describing molecular properties of surfaces for proteins; and
   a server device comprising a computer processor and instructions that, when executed by the computer processor, cause the server device to perform operations comprising:
      receiving, from a computing device, a request to identify a target protein based on a test ligand,
      identifying, using the test ligand and a plurality of docking simulations, a plurality of test-ligand-and-analogous-ligand binding proteins, wherein the plurality of test-ligand-and-analogous-ligand binding proteins are capable of binding with the test ligand and one or more analogous ligands, by:

extracting, from a reference molecular database, molecular data comprising molecular properties of a plurality of ligands;

identifying analogous ligands for the test ligand from the plurality of ligands by comparing the test ligand and the molecular properties of the plurality of ligands;

extracting, from a reference protein database, protein data for a plurality of proteins;

identifying a plurality of analogous-ligand protein complexes by comparing protein data for the plurality of proteins and the analogous ligands, wherein the plurality of analogous-ligand protein complexes comprise a subset of analogous binding proteins from the plurality of proteins, wherein the subset of analogous binding proteins are capable of proteins binding with the analogous ligands; and performing the plurality of docking simulations using the test ligand and the subset of analogous binding proteins to identify the plurality of test-ligand-and-analogous-ligand binding proteins, wherein performing the plurality of docking simulations further comprises:
  simulating docking of the test ligand into the subset of analogous binding proteins to generate docking scores for the subset of analogous binding proteins; and
  comparing the docking scores for the subset of analogous binding proteins to a first predetermined threshold;

generating binding site profiles for the plurality of test-ligand-and-analogous-ligand binding proteins, wherein the binding site profiles comprise molecular properties of the plurality of test-ligand-and-analogous-ligand binding proteins, obtaining the structure data comprising molecular properties of surfaces for the proteins;

comparing the binding site profiles for the plurality of test-ligand-and-analogous-ligand binding proteins with the structure data to identify one or more candidate proteins, performing a docking simulation using the test ligand and the one or more candidate proteins, wherein performing the docking simulation comprises:
  simulating docking of the test ligand into one or more binding sites of the one or more candidate proteins to generate one or more docking scores for the one or more candidate proteins; and
  identifying the target protein from the one or more candidate proteins by comparing the one or more docking scores of the one or more candidate proteins with a second pre-determined threshold;

inserting the target protein into a proteome binding profile of the test ligand;

providing, for display, to one or more client devices, the target protein; and generating, based on the proteome binding profile of the test ligand, a therapeutic treatment utilizing the test ligand.

9. The system of claim 8,
wherein the target protein comprises a plurality of target binding sites, and
wherein the structure data further describes molecular properties of the plurality of target binding sites.

10. The system of claim 9, wherein identifying the target protein further comprises:
  identifying, using the binding site profiles for the plurality of test-ligand-and-analogous-ligand binding proteins and the structure data, a target binding site of the plurality of target binding sites; and
  providing, for display, to the one or more client devices, the target binding site.

11. The system of claim 8, wherein identifying the one or more candidate proteins further comprises:
  generating a similarity measure by comparing the binding site profiles of the plurality of test-ligand-and-analogous-ligand binding proteins to the structure data, and
  determining that the similarity measure exceeds a third pre-determined threshold.

12. The system of claim 8, wherein each protein of the subset of analogous binding proteins comprises a plurality of binding sites.

13. The system of claim 12, wherein instructions capable of performing the plurality of docking simulations further comprises simulating docking of the test ligand with regard to the plurality of binding sites.

14. The system of claim 8, wherein identifying the analogous ligands comprises:
  identifying molecular properties of the test ligand;
  generating a molecular fingerprint based on the molecular properties of the test ligand; and
  using the molecular data, generating molecular fingerprints of each ligand of the plurality of ligands; and
  identifying the analogous ligands based on similarity between the molecular fingerprints of the plurality of ligands and the molecular fingerprint of the test ligand.

15. A non-transitory computer-readable medium comprising instructions that, when executed by at least one computer processor, cause the at least one computer processor to perform operations comprising:
  receiving, from a computing device, a request to identify a target protein based on a test ligand;
  identifying, using the test ligand and a plurality of docking simulations, a plurality of test-ligand-and-analogous-ligand binding proteins, wherein the plurality of test-ligand-and-analogous-ligand binding proteins are capable of binding with the test ligand and one or more analogous ligands, by:
    extracting, from a reference molecular database, molecular data comprising molecular properties of a plurality of ligands;
    identifying analogous ligands for the test ligand from the plurality of ligands by comparing the test ligand and the molecular properties for the plurality of ligands;
    extracting, from a reference protein database, protein data for a plurality of proteins;
    identifying a plurality of analogous-ligand protein complexes by comparing protein data for the plurality of proteins and the analogous ligands, wherein the plurality of analogous-ligand protein complexes comprise a subset of analogous binding proteins from the plurality of proteins, wherein the subset of analogous binding proteins are capable of binding with the analogous ligands; and
    performing the plurality of docking simulations using the test ligand and the subset of analogous binding proteins to identify the plurality of test-ligand-and-analogous-ligand binding proteins, wherein performing the plurality of docking simulations further comprises:

simulating docking of the test ligand into the subset of analogous binding proteins to generate docking scores for the subset of analogous binding proteins; and comparing the docking scores for the subset of analogous binding proteins to a first pre-determined threshold;

generating binding site profiles for the plurality of test-ligand-and-analogous-ligand binding proteins, wherein the binding site profiles comprise molecular properties of the plurality of test-ligand-and-analogous-ligand binding proteins;

obtaining, from a server device, structure data comprising molecular properties of surfaces for proteins;

comparing the binding site profiles for the plurality of test-ligand-and-analogous-ligand binding proteins with the structure data to identify one or more candidate proteins;

performing a docking simulation using the test ligand and the one or more candidate proteins, wherein performing the docking simulation comprises:

simulating docking of the test ligand into one or more binding sites of the one or more candidate proteins to generate one or more docking scores for the one or more candidate proteins; and identifying the target protein from the one or more candidate proteins by comparing the one or more docking scores for the one or more candidate proteins to a second pre-determined threshold;

inserting the target protein into a proteome binding profile of the test ligand;

providing, for display, to one or more client devices, the target protein; and generating, based on the proteome binding profile of the test ligand, a therapeutic treatment utilizing the test ligand.

16. The non-transitory computer-readable medium of claim 15, wherein identifying the analogous ligands comprises:

identifying molecular properties of the test ligand;

generating a molecular fingerprint based on the molecular properties of the test ligand;

using the molecular data, generating molecular fingerprints of each ligand of the plurality of ligands; and identifying the analogous ligands based on similarity between the molecular fingerprints of the plurality of ligands and the molecular fingerprint of the test ligand.

* * * * *